United States Patent [19]

Nelson

[11] Patent Number: 4,565,447
[45] Date of Patent: Jan. 21, 1986

[54] PHOTOMETRIC APPARATUS WITH MULTI-WAVELENGTH EXCITATION

[75] Inventor: Kenneth E. Nelson, N. Attleboro, Mass.

[73] Assignee: Millipore Corporation, Bedford, Mass.

[21] Appl. No.: 553,736

[22] Filed: Nov. 21, 1983

[51] Int. Cl.$^4$ .............................................. G01J 3/42
[52] U.S. Cl. .................................. 356/319; 356/334; 364/498
[58] Field of Search ................... 356/23, 24, 319, 323, 356/325, 326, 328, 331, 332, 334; 364/498, 526

[56] References Cited

U.S. PATENT DOCUMENTS

| | | | |
|---|---|---|---|
| 3,637,310 | 1/1972 | Naono | 356/319 |
| 3,765,769 | 10/1973 | Treacy | 356/328 |
| 3,810,696 | 5/1974 | Hutchins, Jr. | 356/409 |
| 4,322,807 | 3/1982 | Chamran et al. | 364/498 |
| 4,464,051 | 8/1984 | Talmadge et al. | 356/323 |
| 4,482,966 | 11/1984 | Mito et al. | 364/498 |

OTHER PUBLICATIONS

"Scanning System for an Echelle Monochromator," Anderson et al., Anal. Chem., V. 53, No. 6, pp. 770–775, May 1981.
"Multiwavelength Detection for Liquid Chromatography with a Repeat-Scanning Ultraviolet-Visible Spectrophotometer," Saitoh et al., Anal. Chem., V. 51, No. 11, pp. 1683–1687, Sep. 1979.
"Microprocessor Control Automates New HPLC," Karasek, Research/Development, V. 28, No. 6, pp. 38–44, Jun. 1977.
"Computer-Controlled Programmable Monochromator System with Automated Wavelength Calibration and Background Correction," Spillman et al., Anal. Chem., V. 48, No. 2, pp. 303–311, Feb. 1976.
"Design of a Microprocessor-Based Data System for Chromatography," Hendrickson et al., Am Lab., V. 7, No. 9, pp. 100–107, Sep. 1975.

Primary Examiner—F. L. Evans
Assistant Examiner—Joel L. Harringa
Attorney, Agent, or Firm—Andrew T. Karnakis

[57] ABSTRACT

A system for photometric measurement of optical properties of a fluid medium utilizing multi-wavelength excitation includes a movable diffraction grating that is continuously oscillated over the spectral range of interest and a flashlamp producing high intensity, short duration flashes. The angular position of the grating at the time of a flash determines what wavelength of optical energy will be passed to the remainder of the system. Because the flash duration is brief in relation to the period of movement of the grating, the flash effectively freezes the motion of the grating allowing the high intensity output of the flashlamp to be supplied to the fluid medium, while successive flashes permit measurement at many different wavelengths in near simultaneous fashion. The system is disclosed for use in an absorbance detector for liquid chromatography.

15 Claims, 3 Drawing Figures

PHOTOMETRIC APPARATUS WITH MULTI-WAVELENGTH EXCITATION

FIELD OF THE INVENTION

This invention relates generally to photometric apparatus, such as spectrophotometers and spectrofluorometers, and more particularly to such apparatus adapted for use as ultraviolet/visible light absorbance detectors capable of substantially simultaneous monitoring of the absorbance characteristics of fluids at more than one wavelength. Absorbance detectors of this general type are suitable for use in high performance liquid chromatography (HPLC) systems.

BACKGROUND OF THE INVENTION

The term multi-wavelength detector as applied to the art of liquid chromatography and as used throughout this specification refers to an absorbance detector that is capable of "simultaneously" detecting the absorbance characteristics of a sample solution at more than one wavelength. What is meant by the term "simultaneously" is that a series of measurements at different wavelengths are made in a sufficiently short period of time so that only slight concentration changes occur in the sample being analyzed during the period of measurement. This terminology (i.e., multi-wavelength) is to be contrasted with the terms "variable" or "tunable" wavelength detectors which imply an off-line adjustment made to the absorbance detector so that different sample runs can be analyzed at different wavelengths in the range of interest.

In the past, ultraviolet/visible absorbance detectors have been very popular for use with HPLC systems because a significant number of compounds absorb radiation in the ultraviolet/visible range. The majority of these devices operate by analyzing a given sample solution at a single wavelength whether through use of a line emission source in combination with wavelength selective filters or a wide-range continuous source in combination with a monochromator. Problems arise with this measurement technique if some of the compounds being analyzed are only slightly absorbing at the wavelength at which the sample is irradiated. This produces an unacceptably low signal to noise ratio for those compounds.

It should be noted that where absorbance detectors are commonly said to operate at a specific wavelength, in all cases where the source emits a continuum of radiation as opposed to line emissions at fixed wavelengths, the detector is actually operating over a wavelength interval, the extent of which is determined by the spectral bandwidth of the instrument.

In order to improve upon the response of such single wavelength absorbance detectors, and to provide additional information with respect to the compound of interest, it has been proposed to measure absorbance of the sample at different wavelengths, and even to form a ratio of absorbances at different wavelengths, within time intervals short enough to minimize concentration changes in the sample. An example of such a multi-wavelength device is described in an article by Koichi Saltoh and Nobuo Suzuki that appeared in *Analytical Chemistry*, Vol. 51, Number 11, September 1979. The spectrophotometer described there is a dual beam optical instrument capable of scanning wavelengths between 200 and 800 nanometers (nm) which employs two alternate, continuous light sources—a 30 watt deuterium and a 30 watt Tungsten lamp. The wavelength of the monochromator depends on the angular position of a diffraction grating, which is controlled by an electrically driven motor/clutch arrangement. The grating is moved across the full range of the desired spectrum at a rate of either two or one Hz. A shaft encoder senses the angular position of the grating. During each scanning cycle, absorbance data at the desired wavelength is extracted by the photodetector system which includes photo multiplier tubes for appropriate amplification. The short duration during which absorbance is measured at any given wavelength results in only a very limited signal level to be recorded at the photodetectors due to the low radiated power of the lamp. This causes signal to noise ratios to be low, limiting the sensitivity of the measurement.

Another attempt to utilize multi-wavelength absorption detection is found in the Model 165 Multichannel Rapid Scanning UV-Vis Detector manufactured by Beckman Instruments. This device also is a dual beam instrument that uses a conventional deuterium lamp that is continuously energized when the instrument is operated to generate radiation over the wavelength range of interest, but rather than provide a constantly moving diffraction grating, a positioning system is used to rapidly move the grating to an assigned position corresponding to the desired wavelength. This grating position is then maintained for a sufficient period of time to receive enough radiant energy at the photodectors to obtain a usable signal level. However, the low radiant energy output of the deuterium source requires this "holding period" to be sufficiently long to severly limit the number of wavelengths at which absorbance can be measured. Furthermore, due to the short sample measurement duration available if successive measurements are to appear to be simultaneous, it is necessary that the grating be rapidly displaced to the correct position for the next wavelength at which the sample is to be monitored. Thus it is apparent this system involves overcoming a significant amount of inertia in constantly starting, driving and stopping the grating, all of which must be achieved at relatively high speeds. Such a system requires low friction mechanical components and suffers from further difficulties associated with stopping the high speed movement of the grating precisely at the required position without undergoing undesirable oscillations. Moreover, the Beckman system relies upon a closed loop servo positioner and associated sensor to accurately position the grating, all of which adds to the complexity of the detector.

The foregoing examples of prior art multi-wavelength absorbance detectors exhibit certain fundamental operative limitations by using a continuous source in the measurement of more than one wavelength. This results in a tradeoff between the time involved in making the measurement and the amount of radiant energy received at the detector. If the measurement period is made long enough to allow sufficient energy to pass at the wavelength in question and thus increase the signal to noise ratio, either the number of wavelengths that can be measured simultaneously will be limited or fast eluting peaks will not be detected. On the other hand, short measurement period systems have low signal to noise ratios. While high-intensity pulsed sources that operate over a wide wavelength continuum have been proposed in the past (see for example U.S. Pat. No. 3,810,696), such uses have been in single wavelength applications. Moreover an important consideration in this prior patent is to overcome the undesirable heating effects of high power, continuous radiation sources while increasing source intensity.

SUMMARY OF THE INVENTION

The foregoing limitations of prior art absorbance detectors are overcome by the present invention. In a preferred embodiment, a multi-wavelength detector is disclosed having a diffraction grating that is continuously oscillated over the spectral range of interest and a flash tube (preferably xenon) which produces a train of high intensity, short duration flashes. Because the duration of the pulses of radiation is extremely brief (e.g., a few micro seconds) in relation to the speed of movement of the grating, a stroboscopic effect is produced which effectively freezes the motion of the grating during each pulse of light. The angular position of the grating, which is driven by a synchronous motor such as a stepper motor, determines what wavelength will be passed to the detectors. The relationship between motor position and wavelength output is approximated by a sinusoidal function and the time at which a flash occurs is synchronized by a microprocessor which stores the grating position versus output wavelength relation and correspondingly assigns a motor position value to successive wavelength intervals in the lamp spectrum.

In accordance with other features of the embodiment, a dual beam spectrophotometer is provided wherein the source radiation is transmitted to both sample and reference cells adjacent to the detector in a manner that accurately positions each beam at identical locations on the two cells. This is achieved by including a refractive element in the optical path to one of the cells to equalize the effective beam path length with respect to that of the other cell. To align the beam on a desired segment of the reference cell, this refractive element is made adjustable to compensate for manufacturing tolerances within the instrument. Provisions are also included to calibrate the position of the motor (and hence the grating) with the desired wavelength output that utilizes the capabilities of the microprocessor and avoids the need for separate position determination means.

Other aspects and advantages of the present invention will become apparent from the following description of illustrative examples of the invention taken in conjunction with the drawings.

DRAWINGS

DESCRIPTION OF PREFERRED EMBODIMENT

Figure 1:
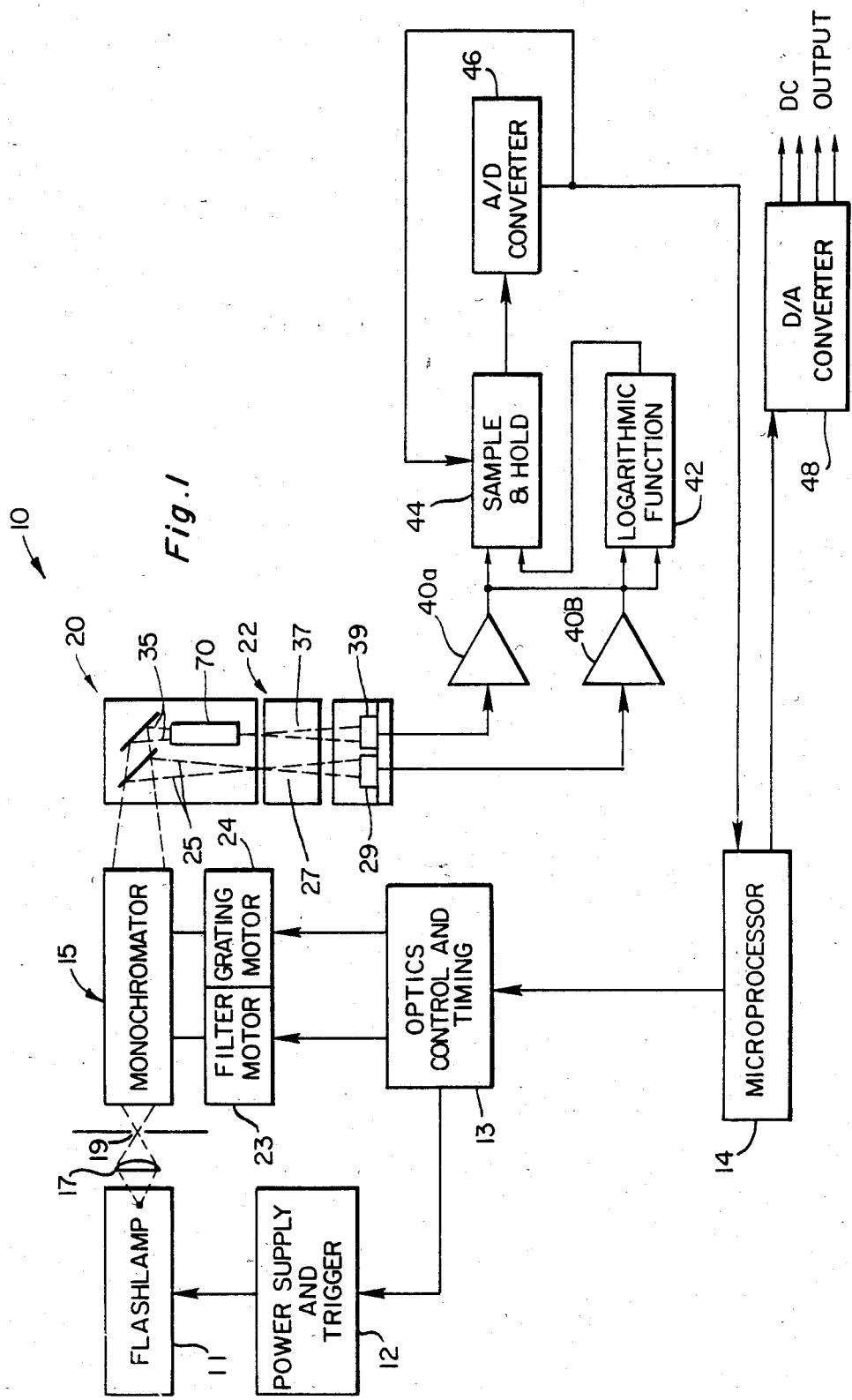
FIG. 1 is a block diagram of a spectrophotometer built in accordance with the present invention.

Referring to FIG. 1, there is shown an absorption detector 10 suitable for use with HPLC systems. The detector includes a xenon flashlamp 11 capable of producing radiation on a pulsed basis over a continuum within the ultraviolet and visible electromagnetic spectrum. A power supply and trigger circuit 12 connected to the flashlamp receives flash command pulses from an optics control and timing circuit 13. The triggering of the voltage pulses is controlled by a microprocessor 14.

Figure 2:
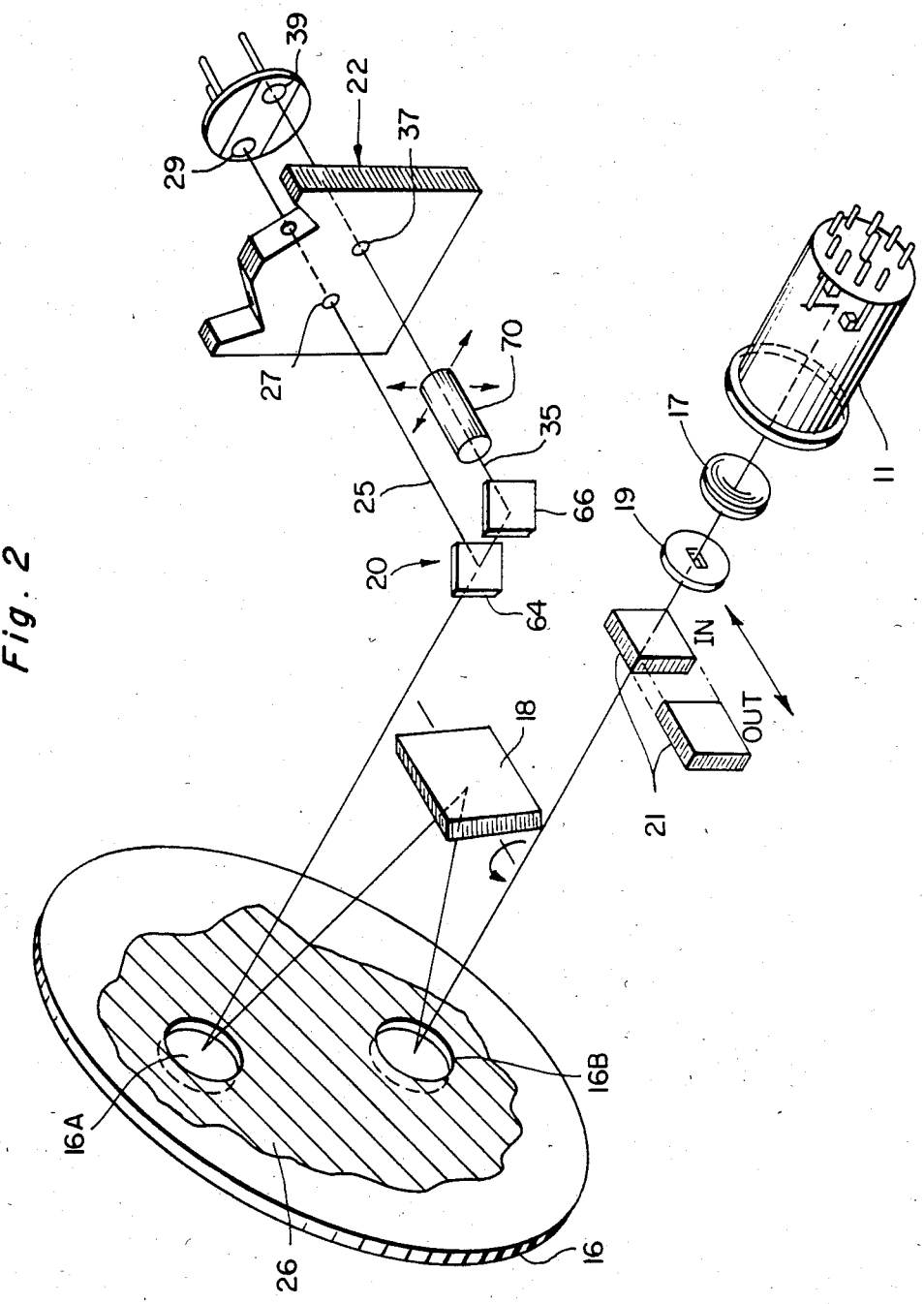
FIG. 2 is a schematic, in semi-pictoral form, of the optical energy transfer portion of the system of FIG. 1.

When energized the flashlamp 11 produces a polychromatic output which enters a monochromator 15 consisting of a spherical mirror 16 and a movable diffraction grating 18 (see also FIG. 2). The output beam of the monochromator is a wavelength band centered about the selected wavelength that corresponds to the angular position of the grating. This output beam is divided into two beams 25, 35 at a beam splitter 20 which directs the split beam in parallel fashion to a flow cell block 22. This block contains a pair of flow cells 27, 37, with the beam 25 propagating through cell 27 to a photodiode 29 and the beam 35 passing through cell 37 to a separate photodiode 39. Each diode output is collected by a respective charge integrator 40A, 40B and supplied to a logarithmic function circuit 42 which takes the logarithmic ratio of the two signals. The output of the circuit 42 is stored in a sample and hold circuit 44, converted to digital format by an analog to digital (A/D) converter 46 and read by the microprocessor 14. The output of the charge integrator 40A is also converted to digital form and similarly read by the microprocessor.

Considering in more detail the operation of the detector 10, particularly the optical energy transfer within the system, reference is specifically made to FIG. 2. The microprocessor 14 sends a command signal to the optics timing and control circuit 13 which enables the power supply and trigger circuit 12 thereby causing the xenon flashlamp 11 to produce very brief (5 microsecond), very intense (22 kilowatt) pulses of light at a rate of 10 pulses per second. A lens 17 forms an image of the arc produced by the flash lamp on an aperture 19 to provide an approximate point source of light. If desired, an order filter 21 driven by a motor 23 under control of the microprocessor can be inserted in the beam path to block wavelengths of the xenon spectrum below a cut off wavelength. The beam from the aperture is directed to the spherical mirror 16 which has an opaque mask 26 covering all but upper and lower reflective portions 16A, 16B respectively. Depending on whether the order filter is in or out of the beam all wavelengths produced by the source are present at and illuminate the lower reflective portion 16B of the mirror which then reflects a substantially collimated beam of light onto the grating 18. A stepper motor 24 through an appropriate linkage (not shown) oscillates the grating 18 continuously back and forth through a range of angular positions that covers the desired usable output wavelength range of the flashlamp. One complete oscillation corresponds to two traversals of this range, one in order of ascending wavelength, the other in descending wavelength. The instantaneous angular position of the grating at the instant a flash occurs (i.e., the flashpoint) determines what wavelength interval will pass through the remainder of the optical system to the photodiodes 29, 39. The beam is diffracted by the grating and is dispersed into a spectrum of radiation, and thereafter directed to the upper reflective portion 16A of the spherical mirror which focuses a selected band of wavelengths through the beam splitter 20. The monochromator described above is commonly referred to as an Ebert monochromator.

The beam splitter 20 divides the incoming beam into the two parallel output beams 25, 35 and directs these beams to the flow cell block 22. Each of these beams impinges on the block at the entrances of each of the respective flow cells 27, 37 and is transmitted therethrough. The cell 27 receives the sample to be analyzed and is normally connected to the outlet of a chromatographic column and thus has the column eluent flowing through it. The other cell 37 serves as a reference and normally contains air but may also contain a flowing fluid similar to that in the sample cell. The flow cell block and related flow cells are of the design described in U.S. Pat. No. 4,011,451 and include tapered flow cells to minimize the interfering effects of refractive index changes for the various liquids whose absorption characteristics are to be measured. If further details are desired on the operation of the flow cell, reference can be made to the aforementioned patent.

After passing through the cells 27, 37 the beams 25, 35 then strike the photodiodes 29, 39 which convert the received optical energy into an electrical signal proportional to the intensity of radiation reaching the photodiodes. Absorption of light by the sample diminishes the intensity at the sample photodiode 29 without affecting the intensity detected by the reference photodiode 39. The logarithmic ratio of these two signals formed in the logarithmic function circuit 42 provides an analog signal representative of the absorbance of the sample at the wavelength corresponding to the angular position of the grating. As mentioned, this signal after appropriate conversion is read by the microprocessor 14 which then supplies a corresponding analog output through a digital to analog (D/A) converter 48.

The brief duration flash makes the moving grating appear to be stationary because the change in angular position of the grating 18 during the duration of the flash is extremely small. Correspondingly, the change in output wavelength due to this movement is negligible in comparison to the spectral bandwidth of the detector. This effect is similar to the apparent stopping of high speed motion by a stroboscope. In this instance, the short duration of the flash effectively freezes the motion of the grating during each pulse of light, while the high instantaneous intensity output of the flashlamp 11 supplies a correspondingly high level of optical energy to the optical system. Thus it is apparent that by properly coordinating the timing of the flash to the motion of the grating, the system can operate at many different desired wavelengths simultaneously with enhanced signal to noise characteristics. This coordination function is controlled by the microprocessor 14 which provides appropriately timed signals to trigger the flash of the xenon flashlamp at the proper position of the stepping motor 24 and hence the grating. The microprocessor stores the absorbance signals measured at each wavelength separately and combines the respective data values to yield essentially a continuous absorbance output for each wavelength measured. Moreover, since the grating is constantly moving, it is possible to measure a plurality of distinct wavelengths without sacrificing the signal to noise ratio.

An important feature of the coordination between the grating position and the flashpoint of the lamp rests in the ability of the detector to calibrate itself with respect to the relationship between the position of the stepper motor 24 and the wavelength of the system. Because the detector system of the embodiment being described does not include a distinct grating position sensor, there is no direct sensing of the position of the stepper motor and thus the angular position of grating. Therefore, the position of the stepper motor must be determined. Once this is done, the position of the motor 24 that corresponds to any given wavelength is known. This is done by taking advantage of the wavelength structure of the flashlamp output whose output continuum is zero below a certain lower wavelength limit and which has several distinctive peak emissions superimposed on a gently varying background. These peaks occur at certain repeatable characteristic wavelengths over the spectrum produced by the flashlamp.

The relationship between the position of the motor 24 as determined by the motor angle within one complete oscillation of the grating and the wavelength output can be approximated by a sinusoidal mathematical function. By utilizing the microprocessor to find and recognize certain characteristics of the xenon flashlamp spectrum by reading the output of the photodiodes, the position of the stepper motor corresponding to known locations in the spectrum can be determined. The actual measured correspondence between a known characteristic (e.g., peak occurrence) and the position of the stepper motor is stored in the memory of the microprocessor and is compared to a table of values representing the mathematical function for those wavelengths in the output continuum where the measured characteristics are expected to occur. The motor position versus wavelength function table is appropriately adjusted with this new value to compensate for any discrepancies between theoretically derived values and actual measurements taken on the particular detector system. Thus, the detector is also self-calibrating.

For the embodiment being described, three features of the xenon flashlamp output energy intensity characteristics are measured, although the principles discussed can be extended to any number of measured characteristics. These are the interval between about 144 and about 185 nanometers (nm) where no energy from the flashlamp 11 reaches the photodiodes 29, 39 due to absorption by the air and the optical elements; the 185 nm point where energy is first sensed by the photodiodes; and the maximum point of the first large peak in the xenon continuum occurring at about 230 nm.

The number of motor steps to produce one complete revolution of the grating is stored in the memory of the microprocessor 14. The microprocessor commands a flashpoint to occur at a predetermined number of steps from the start of a motor revolution. Since on startup the zero energy point ($I_O$) of the continuum is not known, an arbitrary motor step value is selected as the position corresponding to $I_O$. The microprocessor also has stored motor step values corresponding to the total wavelength interval of $I_O$ (e.g., 41 nm), and thus the microprocessor advances the grating and creates a flashpoint in steps that are guaranteed to be less than the $I_O$ interval. The energy reaching the reference photodiode 39 is measured and stored in memory of the microprocessor. After a complete motor revolution, the energy measurements that produced the lowest value are chosen to represent a motor position in the $I_O$ interval. All subsequent energy measurements during the search mode are referenced to this motor step value.

The procedure for locating the motor step values that corresponds to the other two measured energy intensity characteristics of the xenon flashlamp output involve similar techniques of producing flashpoints at a fixed number of motor steps from the $I_O$ point and then reading the output of the reference photodiode 39. Such procedures involve techniques that are well within the skill of a knowledgeable computer programmer and form no part of the present invention and thus will not be explored in any further detail.

When the search mode has been completed, a motor angle corresponding to each measured energy intensity value (e.g., the position of the 230 nm peak in the xenon flashlamp output with respect to the position of the zero energy point) is stored in the microprocessor memory. Thereafter the idealized mathematical function that relates motor step position to wavelength which is tabularized in memory is updated to correspond to the actual measured information. Thus the microprocessor can command a flashpoint to occur at fixed intervals from the $I_O$ point and accurately pass the wavelength of interest to the remainder of the optical system.

Figure 3:
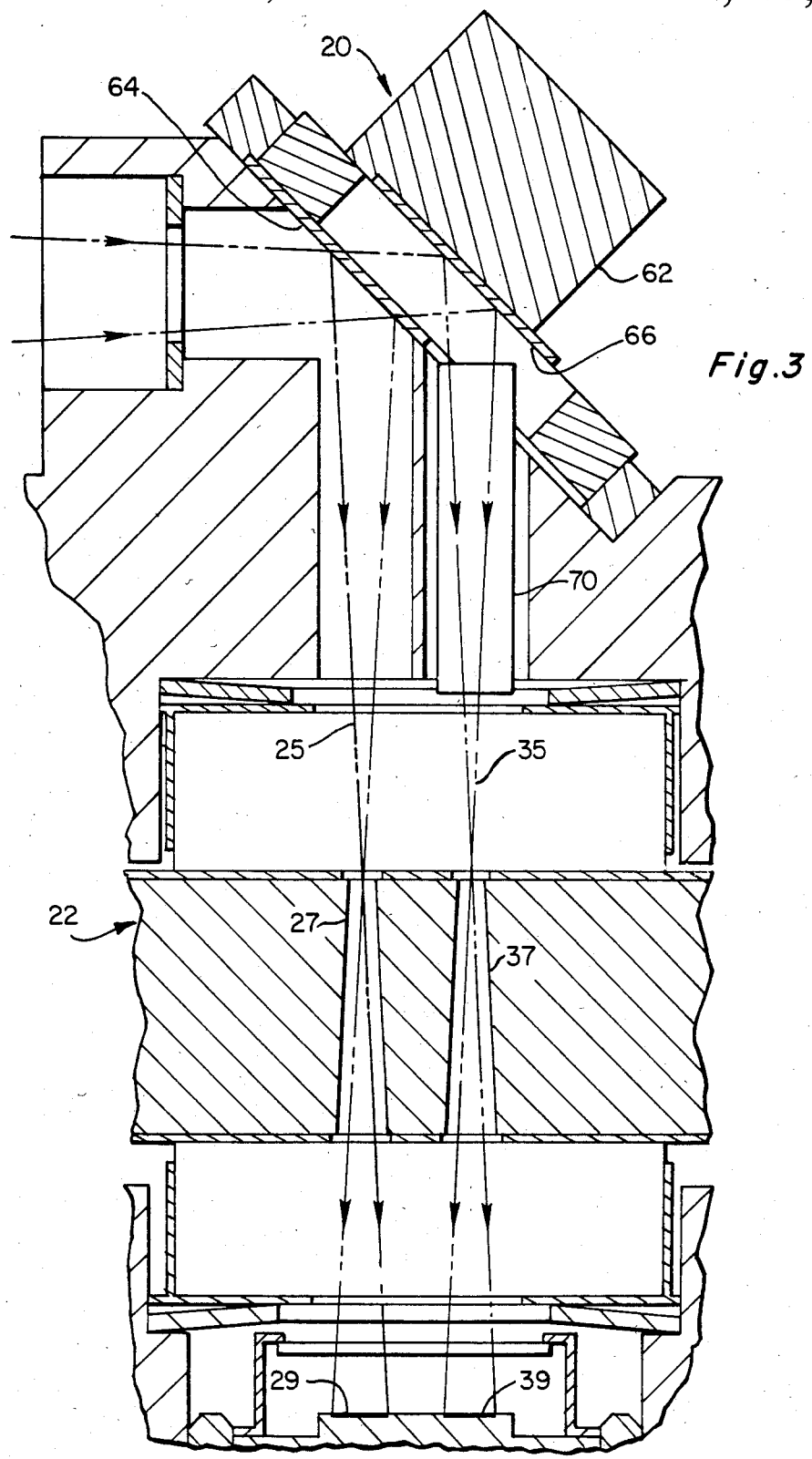
FIG. 3 is a cross sectional view of the beam splitter and sample and reference detection cells for the system of FIG. 1.

FIG. 3 illustrates in further detail the signal detection/conversion portion of the detector 10 which consists of the beam splitter 20, flow cell block 22, and photodiodes 29, 39. The beam splitter is integrally assembled in a housing 62 that is suitably mounted to the flow cell block at the appropriate angle to receive the output wavelength of the monochromator 15 and direct the beams 25, 35 to the sample and reference flow cells 27, 37 respectively. For the sake of clarity these beams are shown as dashed lines. The monochromator output beam is split in the usual manner by including a partially reflecting mirror 64 closest to the input side of the beam splitter and a fully reflecting mirror 66 parallel to and behind the mirror 64.

Since the intensity between successive flashes of the pulses xenon flashlamp 11 can vary, the use of a dual beam system where energy is transmitted both to a sample and a reference cell is useful in compensating for the above variations in intensity of the source. Due to size constraints and other limitations placed upon mechanical tolerances within commercial absorbance detector instruments, difficulties arise in precisely matching each of the two beams which result in reduced signal to noise performance.

Thus a quartz rod 70 is placed in the beam path of the reference beam 35 to equalize the path length of this beam with that of the sample beam 25. In other words, the function of the quartz rod is to make the focal point of the reference beam co-planar with the focal point of the sample beams at the entrance window of the flow cell block. In order to compensate for any misalignment of the various optical components, the quartz rod is pivotally suspended within the support structure to allow for tilting in two orthogonal directions that are in turn perpendicular to the reference beam path. The rod then is caused to move in two directions, i.e., into and out of the plane of the drawing figure and laterally in the plane of the figure. This feature is best illustrated in FIG. 2 by the arrows adjacent the rod 70. Thus it is possible to shift the beam position to coincide with a predetermined location of the reference cell beam entrance window corresponding to a similar location in the sample cell beam entrance window.

Thereafter, the respective beams propagate through each of the cells to the photodetectors. The intensity appearing at the sample cell photodetector is reduced by the amount of energy absorbed by the compounds eluting from the HPLC column that are contained in the sample and an appropriate analog signal is generated by the electrical detection circuitry that is proportional to the amount of absorbance.

Although a preferred embodiment has been set forth in detail above, this is solely for the purpose of illustration as modifications will become apparent to those of skill in the art. For example, the embodiment has been described as operating without the need for a separate positioning system to determine grating position; however, the principles of the present invention can be extended to encompass the inclusion of a position sensor such as a shaft encoder or the like and an appropriate servo-positioner to locate the continuously operated grating at preselected angular positions that are synchronized with the occurrence of a flash. Additionally, the optical excitation means disclosed has been illustrated as operating with an absorbance detector, but these means are equally applicable to a spectrofluorometer. Thus the invention is to be limited only by the scope of the appended claims.

I claim:

1. Apparatus for providing a source of optical energy to a fluid medium and for measuring the optical properties of a sample within said fluid medium comprising:
    a source of radiation capable of producing a continuum of wavelengths over a predetermined range;
    monochromator means having an input for receiving optical energy from said source and an output for producing a corresponding output wavelength interval within the spectral emission of said source;
    motor means for continuously varying the wavelength setting of said monochromator means;
    means for pulsing said source to produce flashes of radiation of output wavelength interval within said spectral emission for transmission to said fluid medium;
    means for synchronizing said pulsing means with said motor means whereby said fluid medium is irradiated with optical energy corresponding to a particular wavelength interval within said spectral emission;
    digital computer means having stored in memory a function representing the output energy intensity produced by said source of radiation over the entire continuum of wavelengths within said predetermined range versus the position of said motor means, said function including at least one uniquely discernible characteristic;
    detector means receiving said flashes of radiation and producing electrical output signals corresponding to the actual output energy intensity from said source;
    said computer means coupled to said pulsing means to produce a series of pulses of radiation to search for said at least one characteristic;
    said computer means coupled to said detector means to receive said electrical output signals thereby determining the position of said motor means which corresponds to said at least one characteristic; and
    means for automatically adjusting said function stored within said memory to correspond to the actual measured motor position of said at least one characteristic.

2. Apparatus as claimed in claim 1 wherein said monochromator means includes a movable diffraction grating and a mirror producing a predetermined series of wavelength intervals within said spectral emission, said predetermined series corresponding to the angular position of said grating at the time of said flashes.

3. Apparatus as claimed in claim 1 wherein said source is a xenon flashlamp emitting radiation over a continuum within the ultraviolet and visible electromagnetic spectrum.

4. Apparatus as claimed in claim 2 wherein said motor means is coupled to said grating to cause continuous oscillation thereof through a range of angular positions corresponding to the continuum produced by said source.

5. Apparatus as claimed in claim 4 wherein said motor means is a stepper motor and said source is a xenon flashlamp emitting radiation in the ultraviolet and visible spectrum.

6. Apparatus as claimed in claim 5 including a beam splitter intermediate said monochromator output and said detector means to form two output beams; a pair of flow cells adjacent said detector means each one of which receives one of said output beams, one flow cell containing a sample fluid whose absorbance is to be measured and the other flow cell containing a reference fluid, said detector means comprising two photodiodes one receiving energy from said sample fluid flow cell, the other receiving energy from said reference fluid flow cell; and means for producing a signal representative of the absorbance only of the sample fluid.

7. Apparatus as in claim 5 wherein the output of said flashlamp is a pulse of energy having a duration short enough with respect to the movement of said grating thereby effectively freezing the motion of said grating during each pulse of energy.

8. A spectrophotometer for detecting the absorbance of light passing through a fluid medium containing a sample to be analyzed comprising:
a source of radiation capable of producing a continuum of wavelengths over a predetermined range;
a diffraction grating adapted to receive an image of said source and to reflect a corresponding spectral emission of said source;
optical means for transfering a wavelength interval within said spectral emission corresponding to the angular position of said grating to said fluid medium;
means for continuously moving said grating through angular positions for producing at said optical means varying wavelength intervals within said spectral emission;
means for pulsing said source for a duration less than the period of movement of said grating;
means to synchronize said pulsing means with said grating moving means whereby the position of said grating when illuminated by said source corresponds to a particular wavelength interval within said spectral emission;
a beam splitter positioned between said optical means and said fluid medium for receiving a beam containing said particular wavelength interval and for producing two corresponding output beams;
a flow cell element containing said fluid medium having first and second co-planar entrance windows, one of said output beams being directed to said first window, the other to said second window; and
means for equalizing the path length of each of said output beams such that the focal points of both are co-planar with said flow cell element entrance windows, said equalizing means comprising a quartz rod positioned in the beam path of one of said output beams.

9. Apparatus as claimed in claim 8 wherein said rod is adjustably supported to allow for displacement in two orthogonal directions perpendicular to the beam path.

10. Apparatus as claimed in claim 8 including a motor coupled to said grating to cause continuous oscillation thereof through a range of angular positions corresponding to the continuum produced by said source.

11. Apparatus as claimed in claim 10 including means for self-calibrating the position of said motor with said particular wavelength interval produced at said optical means at the time of pulsing said source.

12. Apparatus as claimed in claim 11 wherein said self-calibrating means includes digital computer means having stored in memory a function representing the idealized radiation spectrum produced by said source versus the position of said motor and a detector for producing output electrical signals proportional to the actual output radiation from said source, said computer means supplying signals to energize said pulsing means at predetermined positions of said motor and subsequently reading the output of said detector to determine known characteristics of said idealized spectrum at measured motor positions, said computer means comparing said measured positions with said stored function to adjust said function with said measured motor position.

13. A spectrophotometer for detecting the absorbance of light passing through a fluid medium comprising:
a source of radiation producing a continuum of wavelengths over a predetermined range;
monochromator means having an input for receiving optical radiant energy from said source and an output for producing a corresponding output radiant energy wavelength interval within the spectral emission of said source for transmission to said fluid medium;
motor means for continuously varying the wavelength setting of said monochromator means;
digital computer means having stored in memory a function representing the output energy intensity produced by said source of radiation over the entire continuum of wavelengths within said predetermined range versus the position of said motor means, said function including at least one uniquely discernible characteristic;
detector means receiving said radiant energy and producing electrical output signals corresponding to the actual output energy intensity from said source;
said computer means coupled to said motor means to correlate the produced radiant energy with the position of said motor means;
said computer means coupled to said detector means to receive said electrical output signals thereby determining the position of said motor means which corresponds to said at least one characteristic; and
means for automatically adjusting said function stored within said memory to correspond to the actual measured motor position of said at least one characteristic.

14. Appartus as claimed in claim 13 wherein said monochromator means comprises a movable diffraction grating and a mirror producing a predetermined series of wavelength intervals within said spectral emission.

15. Apparatus as claimed in claim 13 further including
a beam splitter for receiving a beam containing said particular wavelength interval and for producing two corresponding output beams;
a flow cell element having first and second co-planar entrance windows, one of said output beams being directed to said first window, the other to said second window; and means for equalizing the path length of each of said output beams such that the focal points of both are co-planar with said flow cell element entrance windows, said equalizing means comprising a quartz rod positioned in the beam path of one of said output beams.

* * * * *